(12) United States Patent
Yamaguchi

(10) Patent No.: US 9,937,216 B2
(45) Date of Patent: Apr. 10, 2018

(54) METHOD FOR SUPPRESSING PROLIFERATION AND/OR INDUCING APOPTOSIS OF CANCER CELLS

(71) Applicant: Maruhachi Muramatsu, Inc., Shizuoka (JP)

(72) Inventor: Masayoshi Yamaguchi, Shizuoka (JP)

(73) Assignee: Maruhachi Muramatsu, Inc., Shizuoka (JP)

( * ) Notice: Subject to any disclaimer, the term of this patent is extended or adjusted under 35 U.S.C. 154(b) by 0 days.

(21) Appl. No.: 15/054,329

(22) Filed: Feb. 26, 2016

(65) Prior Publication Data

US 2017/0246228 A1 Aug. 31, 2017

(51) Int. Cl.
*A61K 36/03* (2006.01)

(52) U.S. Cl.
CPC .................................. *A61K 36/03* (2013.01)

(58) Field of Classification Search
None
See application file for complete search history.

(56) References Cited

U.S. PATENT DOCUMENTS

| | | |
|---|---|---|
| 2013/0259895 A1 | 10/2013 | Yamaguchi |
| 2015/0265663 A1 | 9/2015 | Yamaguchi |

FOREIGN PATENT DOCUMENTS

| | | |
|---|---|---|
| JP | 2003026597 | 1/2003 |
| JP | 2004217559 | 8/2004 |

OTHER PUBLICATIONS

Al Dhaheri (PLoS ONE (2013), vol. 8, No. 7, e68808, pp. 1-17).*
Sestak, "Preventative Therapies for Healthy Women at High Risk of Breast Cancer," Cancer Management and Research, 2014:6, pp. 423-420.

* cited by examiner

*Primary Examiner* — Susan Hoffman
(74) *Attorney, Agent, or Firm* — Occhiuti & Rohlicek LLP

(57) ABSTRACT

It is to provide an agent for suppressing proliferation and/or inducing apoptosis of cancer cells that can be used for the treatment and chemoprophylaxis of cancer, wherein the agent is easily accessible and ingestible in daily dietary life and is prepared using a naturally-derived ingredient with reduced side effects, and a method for suppressing proliferation and/or inducing apoptosis of cancer cells in a subject in need thereof, and the like. By administering an agent for suppressing proliferation and/or inducing apoptosis of cancer cells comprising *Sargassum horneri* or a processed product thereof to a subject in need thereof, the proliferation of cancer cells can be inhibited and apoptosis of cancer cells can be induced in the subject.

6 Claims, 3 Drawing Sheets

METHOD FOR SUPPRESSING PROLIFERATION AND/OR INDUCING APOPTOSIS OF CANCER CELLS

TECHNICAL FIELD

The present invention relates to a method for suppressing proliferation and/or inducing apoptosis of cancer cells in a subject in need thereof, comprising administering a therapeutically effective amount of an agent for suppressing proliferation and/or inducing apoptosis of cancer cells to the subject, wherein the agent for suppressing proliferation and/or inducing apoptosis of cancer cells is *Sargassum horneri* or a processed product thereof. The present invention also relates to an agent for suppressing proliferation and/or inducing apoptosis of cancer cells comprising *Sargassum horneri* or a processed product thereof as an active ingredient.

BACKGROUND ART

Cancer is a disease that is the number one cause of death in developed countries, which is caused by mutations in various cancer genes and cancer-suppressing genes in normal cells. The mutations in cancer genes and cancer-suppressing genes mostly result in the activation of the proliferation signaling and a failure in the apoptosis-regulating signals (inhibition of apoptosis). Further, cancer includes localized types, which are cancers that are limited to the primary lesions, and distant metastatic types, which are cancers that metastasize to other organs. Distant metastatic cancers have much lower 5-year-survival rates than localized cancers.

For example, breast cancer is by far the most common cancer in women worldwide and still ranks second in cancer mortality rates by site in developed countries. Breast cancer is associated with a variety of lifestyle choice, such as obesity, later onset of first childbirth, and the use of hormone replacement therapy (Non-patent Document 1). Breast cancer bone metastasis occurs in 70 to 80% of patients with advanced breast cancer, leading to severe pathological bone fractures, pain, hypercalcemia, and spinal cord and nerve-compression syndromes, which are the primary causes of morbidity and mortality.

Cancer therapies include surgery, radiotherapy, and drug therapy. As described above, because bone metastasis, etc. are highly likely to occur in patients with advanced breast cancer, they are usually treated not only with locoregional therapies such as surgery and radiotherapy, but also with combined systemic therapy such as drug therapy. At this point, drug therapy for breast cancer includes chemotherapy using anticancer drugs, hormonal therapy involving administering antiestrogen agents, etc. for suppressing the action of estrogen, which accelerates the proliferation of breast cancer, and molecularly targeted therapy using drugs that target and attack molecules unique to cancer cells (for example, HER2 protein in breast cancer). Also, means for preventing cancer include improvement in lifestyle habits such as smoking cessation and improvement in diet. Recently, chemoprevention, which involves administering drugs, supplements, vaccines, or other agents to reduce the risk of infection and delay the progression of breast cancer, has been proposed (Non-patent Document 1).

The present inventors have conducted research of various edible marine algae such as *Undaria pinnatifida, Eisenia bicyclis, Gelidium amansii*, and *Ulva pertusa* Kjellman, and proposed a bone mass-increasing composition exerting an antiosteoporotic action comprising, as an active ingredient, a processed product of *Sargassum horneri*, which is known to be marine algae of the genus *Sargassum* in the order Fucales, the prolific brown algae inhabiting shallow seas (Patent Document 1), an agent for preventing or improving diabetic conditions comprising *Sargassum horneri* or a processed product thereof as an active ingredient (Patent Document 2), an NF-κβ inhibitor comprising *Sargassum horneri* or a processed product thereof as an active ingredient (Patent Document 3), and a method for suppressing differentiation of bone marrow mesenchymal stem cells into adipocytes using *Sargassum horneri* or a processed product thereof (Patent Document 4). However, the effects of *Sargassum horneri* or a processed product thereof on cancer cells have not been known to date.

PRIOR ART DOCUMENTS

Patent Documents

[Patent Document 1] Japanese unexamined Patent Application Publication No. 2003-026597
[Patent Document 2] Japanese unexamined Patent Application Publication No. 2004-217559
[Patent Document 3] U.S. Patent Application Publication No. 2013/0259895
[Patent Document 4] U.S. Patent Application Publication No. 2015/0265663

Non-Patent Document

[Non-patent Document 1] Sestak I (2014) Preventative therapies for healthy women at high risk of breast cancer. Cancer Manag Res 6: 423 to 430

SUMMARY OF THE INVENTION

Object to be Solved by the Invention

An object of the present invention is to provide an agent for suppressing proliferation and/or inducing apoptosis of cancer cells that can be used for the treatment and chemoprophylaxis of cancer, wherein the agent is easily accessible and ingestible in daily dietary life and is prepared using a naturally-derived ingredient with reduced side effects, and a method for suppressing proliferation and/or inducing apoptosis of cancer cells in a subject in need thereof, and the like.

Means to Solve the Object

The present inventors have conducted intensive research on the proliferation-inhibiting effects and/or apoptosis-inducing effects of an extract of marine algae *Sargassum horneri* on cancer cells. As a result, they have found that a water extract of *Sargassum horneri* having a molecular weight of 3000 or less shows the proliferation-inhibiting effects and/or apoptosis-inducing effects on cells of MDA-MB-231, which is a cancer cell line derived from human breast cancer cells, thereby completing the present invention.

That is, the present invention relates to the following matters.
(1) A method for suppressing proliferation and/or inducing apoptosis of cancer cells in a subject in need thereof, comprising administering a therapeutically effective amount of an agent for suppressing proliferation and/or inducing apoptosis of cancer cells to the subject, wherein the agent for suppressing proliferation and/or inducing apoptosis of cancer cells comprises *Sargassum horneri* or a processed product thereof.

(2) The method according to the above (1), wherein the processed product of *Sargassum horneri* is an extract of *Sargassum horneri*.

(3) The method according to the above (2), wherein the extract of *Sargassum horneri* is a water extract of *Sargassum horneri*.

(4) The method according to the above (3), wherein the water extract of *Sargassum horneri* is a water extract of *Sargassum horneri* having a molecular weight of 3000 or less.

(5) The method according to the above (1), wherein the cancer cell is a cancer cell of one or more cancers selected from esophageal cancer, stomach cancer, liver cancer, biliary tract cancer, pancreatic cancer, colorectal cancer, breast cancer, lung cancer, each type of bone and soft tissue sarcoma, prostate cancer, bladder cancer, testicular cancer, kidney cancer, renal pelvis and ureter cancer, penile cancer, retroperitoneal tumor, adrenal gland cancer, head and neck cancer, thyroid cancer, uterine cancer, and ovarian cancer.

(6) The method according to the above (5), wherein the cancer cell is a cancer cell of breast cancer.

(7) The method according to the above (1), wherein the subject is one or more selected from a mouse, a rat, a bird, a pig, a sheep, a cow, a cat, a dog, primates, and a human.

(8) The method according to the above (1), wherein the subject is a human.

(9) The method according to the above (1), wherein the subject is a subject with cancer.

(10) The method according to the above (1), wherein the subject is a subject without cancer.

Effect of the Invention

Since the method for suppressing proliferation and/or inducing apoptosis of cancer cells of the present invention is a method employing an agent for suppressing proliferation and/or inducing apoptosis of cancer cells obtainable through extraction and purification from natural products having a long history as food, the method is highly safe and oral administration is possible, and moreover, it can be administered continuously for a long time for prophylactic purposes, thereby bringing about excellent effects.

MODE FOR CARRYING OUT THE INVENTION

Figure 1A:
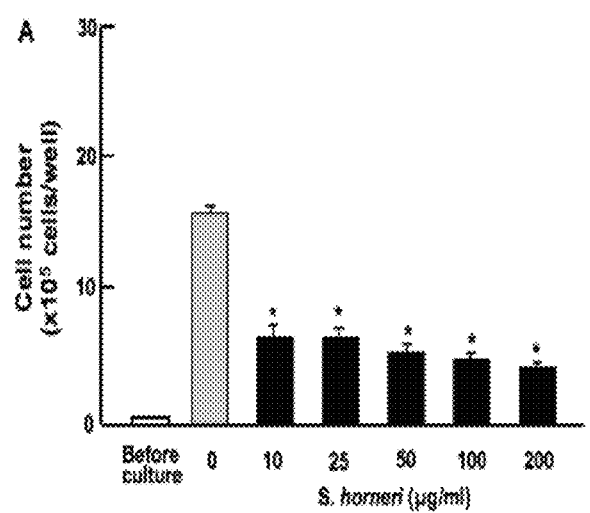
FIG. 1(A) and FIG. 1(B) are a set of graphs showing the number of adherent MDA-MB-231 cells after culture, wherein MDA-MB-231 cells were cultured in Dulbecco's Modified Eagle Medium (DMEM) containing a water extract of *Sargassum horneri* at each concentration of 0, 10, 25, 50, 100, or 200 μg/mL culture solution for 5 days (FIG. 1(A)) or 10 days FIG. 1(B)). In the graphs, "*" indicates that there is a statistical significance (P<0.05) in comparison with a group containing no water extract of *Sargassum horneri* (second from left).

The method for suppressing proliferation and/or inducing apoptosis of cancer cells in a subject in need thereof of the present invention is not particularly limited as long as it is a method comprising administering a therapeutically effective amount of an agent for suppressing proliferation and/or inducing apoptosis of cancer cells to a subject in need thereof, wherein the agent for suppressing proliferation and/or inducing apoptosis of cancer cells is *Sargassum horneri* or a processed product thereof. Examples of *Sargassum horneri* or a processed product thereof include a water extract of *Sargassum horneri* obtained by separating a soluble component using water such as normal temperature water, hot water, and deionized water, an organic solvent extract of *Sargassum horneri* obtained by separating a soluble component using an organic solvent such as aqueous alcohol and hexane, a dried product of *Sargassum horneri* obtained by drying whole *Sargassum horneri*, a dried powder of *Sargassum horneri* obtained by powderizing dried *Sargassum horneri*, and an enzyme-treated product of *Sargassum horneri* obtained by treating *Sargassum horneri* with an enzyme such as cellulase. Among them, a water extract of *Sargassum horneri* and an organic solvent extract of *Sargassum horneri* are preferable, of which a preferable example is a water extract of *Sargassum horneri*.

The agent for suppressing proliferation and/or inducing apoptosis of cancer cells of the present invention is not particularly limited as long as it is an agent that comprises *Sargassum horneri* or a processed product thereof as an active ingredient. Although the aforementioned water extract of *Sargassum horneri* and organic solvent extract of *Sargassum horneri* can be directly used as an active ingredient of an agent for suppressing proliferation and/or inducing apoptosis of cancer cells, it is also possible to fractionate the extract by appropriate purification means such as silica gel column chromatography, reverse phase column chromatography, gel filtration chromatography, and membrane filtration, and use a fraction having higher activities of suppressing proliferation and/or inducing apoptosis of cancer cells. Preferably, as a fraction having higher activities of suppressing proliferation and/or inducing apoptosis of cancer cells, an example is a fraction having a molecular weight of 30000 or less, a preferable example is a fraction having a molecular weight of 10000 or less, a more preferable example is a fraction having a molecular weight of 5000 or less, and an even more preferable example is a fraction having a molecular weight of 3000 or less.

Examples of a method for preparing Sargassum horneri or a processed product thereof include the following methods: That is, a method for preparing an organic solvent extract of Sargassum horneri or a water extract of Sargassum horneri, comprising crushing fresh Sargassum horneri washed with water with a homogenizer and the like, adding to the resultant an approximately 1 to 5 times, preferably approximately 2 to 4 times, particularly preferably approximately 3 times the amount of water such as normal temperature water, hot water, and deionized water or approximately 5 to 80%, preferably approximately 10 to 40%, more preferably approximately 20% of various organic solvents such as aqueous alcohol such as methanol, ethanol, and propanol or hexane for extraction, and carrying out centrifugation for approximately 5 to 15 minutes, preferably approximately 10 minutes at 4000 to 7000 g, preferably 5000 to 6000 g to separate a soluble fraction, and a method comprising drying fresh Sargassum horneri washed with water by freeze vacuum drying, sun drying, air drying, hot air drying, heat drying, microwave drying, and the like. A preferable example is a method comprising adding approximately 3 times the amount of water to crushed Sargassum horneri for extraction, followed by centrifugation for approximately 10 minutes at 5000 to 6000 g to thereby separate a soluble fraction. Also, as Sargassum horneri used for extraction, intact Sargassum horneri that has not been crushed can also be used, and in this case, it is preferable to crush Sargassum horneri with a homogenizer and the like after extraction. Also, when Sargassum horneri is not processed immediately after harvesting, it is preferably preserved at a low temperature of 10° C. or less, for example, 4 to 5° C.

The subject in need according to the present invention is not particularly limited as long as it is a subject in need of suppression of proliferation and/or induction of apoptosis of cancer cells. Although the subject can be a subject suffering from cancer, it is also possible to administer an agent for suppressing proliferation and/or inducing apoptosis of cancer cells to a subject not suffering from cancer for prophylactic purposes. Also, the subject is preferably one or more selected from a mouse, a rat, a bird, a pig, a sheep, a cow, a cat, a dog, primates, and a human, and the subject is more preferably a human.

The cancer cell according to the present invention can be a cancer cell of any cancer, for example, esophageal cancer, stomach cancer, liver cancer, biliary tract cancer, pancreatic cancer, colorectal cancer, breast cancer, lung cancer, each type of bone and soft tissue sarcoma, prostate cancer, bladder cancer, testicular cancer, kidney cancer, renal pelvis and ureter cancer, penile cancer, retroperitoneal tumor, adrenal gland cancer, head and neck cancer, thyroid cancer, uterine cancer, and ovarian cancer. A preferable example is a cancer cell of breast cancer.

The therapeutically effective amount of the agent for suppressing proliferation and/or inducing apoptosis of cancer cells of the present invention is not particularly limited as long as it is such an amount that can bring about the action of suppressing proliferation and/or inducing apoptosis of cancer cells in a subject in need. For example, in the case of a water extract of Sargassum horneri (dry weight), the daily dose is in a range of 0.1 to 1000 mg/kg body weight, preferably in a range of 1 to 100 mg/kg body weight, and in the case of a dried product of Sargassum horneri, the daily dose is in a range of 1 mg to 5 g/kg body weight, preferably in a range of 10 to 1000 mg/kg body weight. Further, dosage can be adjusted as appropriate according to the symptoms, sex, age, and the purpose of administration (treatment or prevention), and the like.

Examples of the dosage form of the agent for suppressing proliferation and/or inducing apoptosis of cancer cells of the present invention include oral administration, in which the agent is administered in the form of a powder, a granule, a tablet, a capsule, a syrup, a suspension, and the like, and injection, in which the agent is administered in the form of a solution, an emulsion, a suspension, and the like. Also, the agent for suppressing proliferation and/or inducing apoptosis of cancer cells of the present invention can be administered as a pharmaceutical product or supplement which is useful for the treatment and prophylaxis of cancer, or serve as a raw pharmacological composition material in such a way the agent is added to and formulated into food, whereby the food can be provided as a functional food having cancer-preventing or improving actions.

When the agent for suppressing proliferation and/or inducing apoptosis of cancer cells of the present invention is used as a pharmaceutical product or supplement, various formulation components such as a pharmaceutically acceptable common carrier, a binder, a stabilizer, an excipient, a diluent, a pH buffer, a disintegrator, a solubilizer, a solubilization aid, and an isotonic agent can be added. Also, when the agent for suppressing proliferation and/or inducing apoptosis of cancer cells of the present invention is used as a raw pharmacological composition material, the agent for suppressing proliferation and/or inducing apoptosis can be added and formulated during the production process or after the production of functional foods.

Specific examples of the aforementioned functional food include various beverages such as yogurt, drinkable yogurt, juice, milk, soymilk, alcoholic beverages, coffee, black tea, green tea, oolong tea, and a sports drink, bread and confectionery such as pudding, cookies, bread, cake, jelly, baked snacks such as a Japanese rice cracker, Japanese traditional confectionery such as yokan (jelly made of sweet bean paste), a refrigerated or frozen dessert, and a chewing gum, noodles such as udon noodles (wheat noodles) and soba noodles (buckwheat noodles), a fish meat paste product such as kamaboko (Japanese fish loaf), ham, and fish meat sausage, seasonings such as miso, soy sauce, dressing, mayonnaise, and a sweetener, a dairy product such as cheese and butter, tofu, konjac, and also, various delicatessens such as tsukudani (food simmered in soy sauce), a dumpling, a croquette, and salad, and various beverages such as yogurt, drinkable yogurt, juice, milk, soymilk, alcoholic beverages, coffee, black tea, green tea, oolong tea, and a sports drink.

The agent for suppressing proliferation and/or inducing apoptosis of cancer cells of the present invention can be used in the production of cancer-preventing or improving feed. By incorporating Sargassum horneri or a processed product thereof, the cancer-preventing or improving feed can be prepared as feed for a mouse, a rat, a bird, a pig, a sheep, a cow, a cat, a dog, primates, and the like, in more detail, feed for livestock such as a pig, a sheep, and a cow, feed for poultry such as a chicken, feed for a cat, a dog, and the like, and laboratory feed for a mouse, a rat, and the like. The feed into which Sargassum horneri or a processed product thereof is incorporated as an active ingredient is useful for the prevention and improvement of cancer in livestock, poultry, pets, and laboratory animals.

Examples of a method for confirming whether or not a test substance has a proliferation-inhibiting action on cancer cells include a method comprising culturing a cancer cell line in a culture solution in the presence or absence of a test substance, followed by counting the number of cells formed, and determining that the test substance has a proliferation-inhibiting action on cancer cells when the number of cells in the presence of the test substance is significantly lower than the number of cells in the absence of the test substance.

Examples of a method for confirming whether or not a test substance has an apoptosis-inducing action on cancer cells include a method comprising culturing a cancer cell line to confluency in a culture solution in the absence of a test substance, and further culturing the cancer cell line in a culture solution in the presence or absence of a test substance, followed by counting the number of cells formed, and determining that the test substance has an apoptosis-inducing action on cancer cells when the number of cells in the presence of the test substance is significantly lower than the number of cells in the absence of the test substance. Alternatively, it is also possible to subject cancer-derived culture cells that are cultured to confluency to additional culture in a culture solution containing a test substance, and further, an apoptosis inhibitor, and determining that the test substance has an apoptosis-inducing action when the number of cells is significantly higher than the number of cells cultured in a culture solution containing no apoptosis inhibitor.

The cancer cell line according to the present invention can be derived from any cancer such as breast cancer, esophageal cancer, stomach cancer, liver cancer, biliary tract cancer, pancreatic cancer, colorectal cancer, lung cancer, each type of bone and soft tissue sarcoma, prostate cancer, bladder cancer, testicular cancer, kidney cancer, renal pelvis and ureter cancer, penile cancer, retroperitoneal tumor, adrenal gland cancer, head and neck cancer, thyroid cancer, uterine cancer, and ovarian cancer. Preferable examples include a cancer cell line derived from breast cancer, and more preferable examples include a cancer cell line selected from MCF-7, HBC-4, BSY-1, HBC-5, and MDA-MB-231.

Hereinbelow, the present invention will be more specifically described with reference to Examples. However, the technical scope of the present invention is not limited to these Examples.

EXAMPLES

Example 1

1. Materials
1-1 Preparation of a Water Extract of *Sargassum horneri*

Marine algae *Sargassum horneri* were harvested at the coasts of Shimoda city, Shizuoka prefecture and Miyako city, Iwate prefecture. *Sargassum horneri* was washed with water and homogenized (crushed) in purified distilled water, followed by centrifugation at 5500 g for 10 minutes. The resulting supernatant solution was freeze-dried as a water-soluble extract of *Sargassum horneri*. The freeze-dried water-soluble extract of *Sargassum horneri* was dissolved in purified distilled water, and a fraction having a molecular weight of 3000 or less was separated by membrane fractionation, whereby a water extract of *Sargassum horneri* was prepared. The water extract of *Sargassum horneri* thus obtained was freeze-dried, which was dissolved in purified distilled water as it was used for experiments.

1-2 Cancer Cell

As the cancer cell, MDA-MB-231 cells were used, which were cultured cells derived from human mammary gland cancer cells (obtained from American Type Culture Collection (ATCC), Rockville, Md., U.S.A.).

Example 2

2. The Action of the Water Extract of *Sargassum Horneri* on Cell Proliferation
2-1 Method
2-1-1 Cell Culture Breast cancer MDA-MB-231 cells ($1 \times 10^5$/ml per well) were cultured in a 24-well plate in DMEM containing 10% FBS and 1% P/S in the presence or absence of *S. horneri* active component (less than 3000 MW; 10, 25, 50, 100 or 200 µg/ml) for 5 and 10 days in a water-saturated atmosphere containing 5% $CO_2$ and 95% air at 37° C.

2-1-2 Counting the Number of Cells

Cells were detached from each culture dishes using 0.2% trpysin plus 0.02% EDTA in $Ca^{2+}$/$Mg^{2+}$-free PBS for 2 min at 37° C., cells were collected after centrifugation. Cells were resuspended on PBS solution and stained with eosin. Cell numbers were counted under a microscope using a Hemocytometer plate. For each dish, we took the average of two countings. Cell number showed as number per well of plate.

2-1-3 Statistical Processing

Data are expressed as the mean±standard deviation (SD). Statistical significance was determined using GraphPad InStat version 3 for Windows XP (GraphPad Software Inc. La Jolla, Calif.). Multiple comparisons were performed by one-way analysis of variance (ANOVA) with Tukey-Kramer multiple comparisons post-test for parametric data as indicated. Data indicated $P<0.05$ was considered statistically significant.

2-2 Results

Figure 1B:
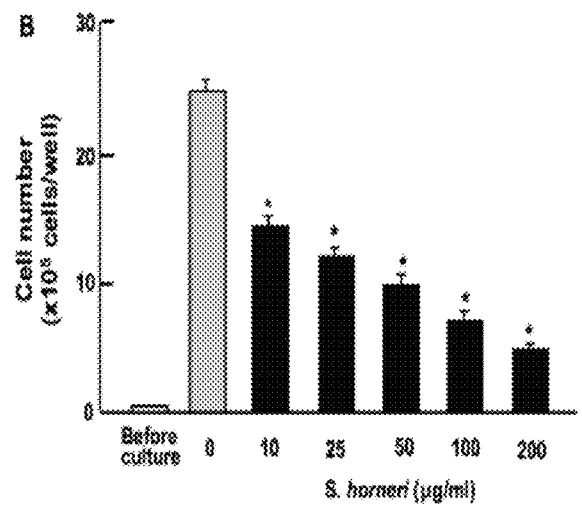

Number of human breast cancer MDA-MB-231 bone metastatic cells was increased with periods of culture in the presence of FBS. Presence of *S. horneri* active component (less than MW 3,000; 10-200 µg/ml) was found to suppress proliferation in human breast cancer MDA-MB-231 cells cultured for 5 FIG. 1(A) and 10 (FIG. 1(B)) days in vitro. Thus, *S. horneri* active component was found to possess suppressive effects on cell proliferation.

Example 3

3. Action of Inhibitors that Induce Cell-Cycle Arrest on Inhibition of Cell Proliferation by the Water Extract of *Sargassum Horneri*
3-1 Method Breast cancer MDA-MB-231 cells ($1 \times 10^5$/ml per well) were cultured in a 24-well plate in DMEM containing 10% FBS and 1% P/S for 3 days in the presence or absence of *S. horneri* active component (50 µg/ml) with or without sodium butyrate (10 and 100 µM), roscovitine (10 and 100 nM) or sulforaphane (1 and 10 nM). Upon completion of culture, the cells were detached from wells, and the number of cells was counted and statistical processing was performed in accordance with the methods described in 2-1-2 and 2-1-3.

3-2 Results

Suppressive effects of *S. horneri* active component on proliferation in MDA-MB-231 cells were determined in the presence of various inhibitors that induce cell-cycle arrest in vitro. Cells were cultured for 3 days in the absence (FIG. 2(A)) or presence (FIG. 2(B)) of *S. horneri* active component (50 µg/ml) with or without butyrate (10 and 100 µM), roscovitine (10 and 100 nM) or sulforaphane (1 and 10 nM).

Figure 2A:
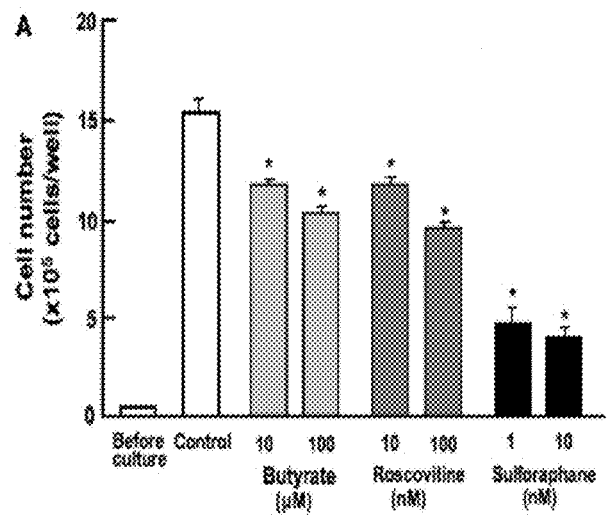
FIG. 2(A) and FIG. 2(B) are a set of graphs showing the number of adherent MDA-MB-231 cells after culture, wherein, in FIG. 2(A), MDA-MB-231 cells were cultured for 3 days in DMEM containing a water extract of *Sargassum horneri* at 50 μg/mL culture solution and an inhibitor that induces cell-cycle arrest (butyrate, roscovitine, or sulforaphane), and in FIG. 2(B), MDA-MB-231 cells were cultured for 3 days in DMEM not containing a water extract of *Sargassum horneri*, but containing an inhibitor that induces cell-cycle arrest (butyrate, roscovitine, or sulforaphane). In the graphs, "*" indicates that there is a statistical significance (P<0.05) in comparison with a group containing no inhibitor that induces cell-cycle arrest (second from left).
Figure 2B:
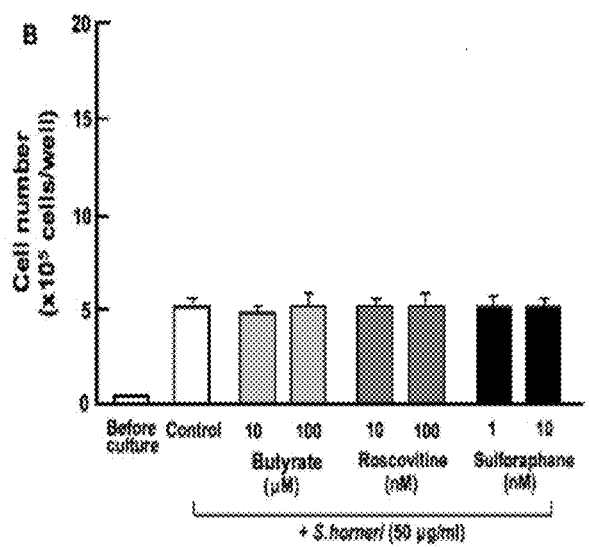

Proliferation of MDA-MB-231 cells was suppressed in the presence of these inhibitors (FIG. 2(A)). Suppressive effects of *S. horneri* active component on cell proliferation were not potentiated in the presence of these inhibitors (FIG. 2(B)).

Example 4

4. Study on the Apoptosis-Inducing Effect of the Water Extract of *Sargassum Horneri*

4-1 Method

Breast cancer MDA-MB-231 cells ($1\times10^5$/ml per well) were cultured using a 24-well plate in DMEM containing 10% FBS and 1% P/S in the absence of *S. horneri* component for 5 days when reached to confluent, and then the cells were cultured in the presence of *S. horneri* component (less than 3000 MW; 10, 25, 50, 100 or 200 µg/ml) for 2 days. In separate experiments, cells were culture for 5 days without *S. horneri*, and then cells were cultured for 2 days in the presence of *S. horneri* (50 µg/ml) with or without caspase-3 inhibitor (5 µM). Upon completion of culture, the cells were detached from wells, and the number of cells was counted and statistical processing was performed in accordance with the methods described in 2-1-2 and 2-1-3.

4-2 Results

Figure 3A:
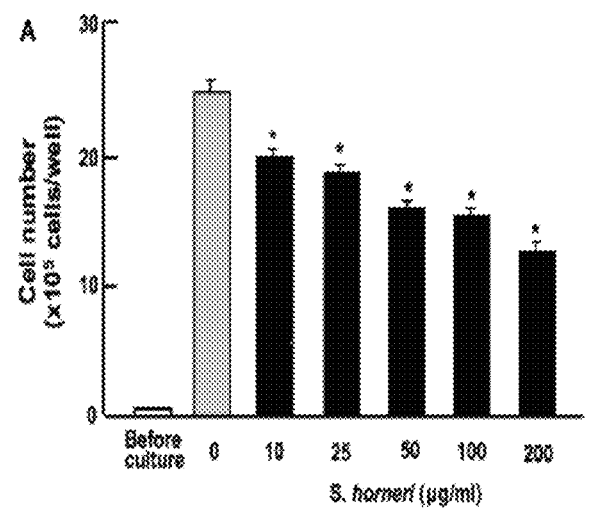
FIG. 3(A) is a graph showing the number of adherent MDA-MB-231 cells, wherein MDA-MB-231 cells were cultured for 5 days to confluency, and then for additional 2 days in DMEM containing a water extract of *Sargassum horneri* at each concentration of 0, 10, 25, 50, 100, or 200 μg/mL culture solution. In the graph, "*" indicates that there is a statistical significance (P<0.05) in comparison with a group containing no water extract of *Sargassum horneri* (second from left).
Figure 3B:
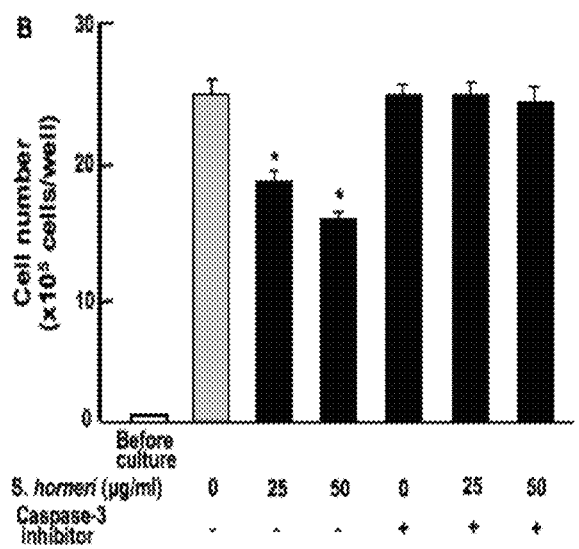
FIG. 3(B) is a graph showing the number of adherent MDA-MB-231 cells, wherein MDA-MB-231 cells were cultured for 5 days to confluency, and then for an additional 2 days in DMEM containing a water extract of *Sargassum horneri* at each concentration of 0, 25, or 50 μg/mL culture solution with (+) or without (−) caspase-3 inhibitors. In the graph, "*" indicates that there is a statistical significance (P<0.05) in comparison with a group containing no water extract of *Sargassum horneri* (second from left).

Human breast cancer MDA-MB-231 cells were cultured for 5 days when reached to confluent, and then the cells were cultured for an additional 2 days in the presence of *S. horneri* active component (less than 3000 MW; 10-250 µg/ml). Cell number was decreased by addition of *S. horneri* active component (FIG. 3(A)). Stimulatory effects of *S. horneri* active component (25 or 50 µg/ml) on cell death in MDA-MB-231 cells were blocked in the presence of caspase-3 inhibitor (5 µM) in vitro (FIG. 3(B)). Thus, culture with *S. horneri* active component stimulated apoptotic cell death in breast cancer MDA-MB-231 cells in vitro.

5. Discussion

Marine algae *S. horneri* active component was found to suppress proliferation and stimulate apoptotic cell death in human breast cancer MDA-MB-231 bone metastatic cells in vitro. This finding demonstrates that *S. horneri* possesses an anticancer effect in MDA-MB-231 cells in vitro. This was the first time finding.

INDUSTRIAL APPLICABILITY

The present invention can prevent or treat cancer by inhibiting the proliferation and inducing apoptosis of cancer cells by using marine algae *Sargassum horneri* or a processed product thereof, particularly an extract of *Sargassum horneri* having a molecular weight of 3000 or less as an active ingredient. Further, because the processed product is prepared from *Sargassum horneri*, which is marine algae with a long history as food, it is highly safe and can be consumed on a daily basis for prophylactic purposes from young age. It is therefore expected to make a contribution to not only healthy elderly living of each individual, but also reduction of medical cost in the aging society.

The invention claimed is:

1. A method for the treatment of cancer in a subject, the method comprising administering, to the subject, a therapeutically effective amount of an agent comprising *Sargassum horneri* or a processed product thereof, wherein the cancer is a breast cancer, wherein the subject is a subject with cancer.

2. The method according to claim 1, wherein the processed product of *Sargassum horneri* is an extract of *Sargassum horneri*.

3. The method according to claim 2, wherein the extract of *Sargassum horneri* is a water extract of *Sargassum horneri*.

4. The method according to claim 3, wherein the water extract of *Sargassum horneri* is a water extract of *Sargassum horneri* having a molecular weight of 3000 or less.

5. The method according to claim 1, wherein the subject is a mouse, a rat, a bird, a pig, a sheep, a cow, a cat, a dog, or a primate.

6. The method according to claim 5, wherein the primate is a human.

* * * * *